(12) United States Patent
Hung et al.

(10) Patent No.: US 10,137,090 B2
(45) Date of Patent: Nov. 27, 2018

(54) NOZZLE, APPARATUS, AND METHOD FOR PRODUCING MICROPARTICLES

(71) Applicant: METAL INDUSTRIES RESEARCH & DEVELOPMENT CENTRE, Kaohsiung (TW)

(72) Inventors: Cheng-Han Hung, Kaohsiung (TW); Zong-Hsin Liu, Kaohsiung (TW); Ying-Chieh Lin, Kaohsiung (TW); Ming-Fang Tsai, Kaohsiung (TW); Hai-Ching Tsou, Kaohsiung (TW); Ying-Cheng Lu, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 0 days.

(21) Appl. No.: 15/378,332

(22) Filed: Dec. 14, 2016

(65) Prior Publication Data

US 2018/0161278 A1  Jun. 14, 2018

(51) Int. Cl.
*A61K 9/16* (2006.01)
*B01J 2/06* (2006.01)
*B01J 2/18* (2006.01)
*B01J 13/08* (2006.01)
*B01J 13/20* (2006.01)

(52) U.S. Cl.
CPC .......... *A61K 9/1682* (2013.01); *A61K 9/1635* (2013.01); *B01J 13/08* (2013.01); *B01J 13/20* (2013.01)

(58) Field of Classification Search
None
See application file for complete search history.

(56) References Cited

U.S. PATENT DOCUMENTS

| 3,933,955 A | * | 1/1976 | Lysher | ........................ B01J 2/08 264/13 |
| 4,251,195 A | * | 2/1981 | Suzuki | ...................... A61J 3/07 264/7 |
| 5,040,960 A | * | 8/1991 | Shioya | ...................... A23L 2/00 264/14 |

(Continued)

FOREIGN PATENT DOCUMENTS

CN  101693177 A  4/2010
CN  103025417 A  4/2013

*Primary Examiner* — Mary Lynn F Theisen
(74) *Attorney, Agent, or Firm* — Alan D. Kamrath; Kamrath IP Lawfirm, P.A.

(57) ABSTRACT

A nozzle, an apparatus, and a method for producing dual-layer microparticles used as microcarriers. The nozzle includes a nozzle body having a first fluid passageway and a cover mounted to the nozzle body and having a second fluid passageway. A plurality of extension tubes is communicated with an end of the first fluid passageway and is spaced from each other. Each extension tube includes an outlet port distant to the first fluid passageway. A plurality of sleeves is communicated with the second fluid passageway. Each sleeve includes an opening distant to the second fluid passageway. Each extension tube extends into one of the sleeves. An outer wall of each extension tube is spaced from an inner wall of one of the sleeves. The outlet port of each extension tube is located between the second fluid passageway and the opening of one of the sleeves.

19 Claims, 11 Drawing Sheets

(56) References Cited

U.S. PATENT DOCUMENTS

| | | | | |
|---|---|---|---|---|
| 5,888,538 A | * | 3/1999 | Kiefer | B01J 2/003 264/4 |
| 2011/0212203 A1 | * | 9/2011 | Ikeda | A61J 3/07 425/10 |
| 2012/0156490 A1 | * | 6/2012 | Fournier-Bidoz | C40B 20/04 428/402 |
| 2013/0119570 A1 | | 5/2013 | Sugiura et al. | |

* cited by examiner

NOZZLE, APPARATUS, AND METHOD FOR PRODUCING MICROPARTICLES

BACKGROUND

1. Technical Field

The present disclosure relates to a nozzle, an apparatus, and a method for producing microparticles and, more particularly, to a nozzle, an apparatus, and a method for mass production of dual-layer microparticles used as microcarriers.

2. Description of the Related Art

Microparticles, also known as microspheres, are spherical particles having a diameter ranging from 1 µm to 1000 µm, are generally used as microcarriers for releasing drug, and have become one of the emerging drug delivery technologies due to the characteristics of targeting, controlled release, stability, and surface modifiability.

Since the diameters of microparticles are small, the first aim is to form microparticles of uniform diameters to make each microparticle have the same drug releasing effect. For example, a conventional micro fluid passageway structure 9 shown in FIG. 1 can be used to form microparticles with more uniform diameters.

With reference to FIG. 1, the conventional micro fluid passageway structure 9 includes a Y-shaped passageway 91, a curing agent filling port 92, a material solution filling port 93, and a cruciform micro fluid passageway 94. The Y-shaped passageway 91 is intercommunicated with the cruciform micro fluid passageway 94. A branch of the Y-shaped passageway 91 is intercommunicated with the curing agent filling port 92 through which a curing agent solution is filled. Another branch of the Y-shaped passageway 91 is intercommunicated with the material solution filling port 93 through which a material solution is filled. The curing agent solution and the material solution form a pre-solidified mixed solution at a third end of the Y-shaped passageway 91. The third end of the Y-shaped passageway 91 is intercommunicated with the cruciform micro fluid passageway 94. A water phase solution is filled through two ends of the cruciform micro fluid passageway 94. The shear stress of the water phase solution filled into the cruciform micro fluid passageway 94 makes the pre-solidified mixed solution flowing into the cruciform micro fluid passageway 94 form emulsified spheres separate from each other, and each emulsified sphere finally forms a microparticle.

Although the above conventional micro fluid passageway structure 9 can form microparticles with more uniform diameters, the conventional micro fluid passageway structure 9 cannot easily proceed with mass production. Improvement is, thus, necessary.

SUMMARY

To solve the above problem, the present disclosure provides a nozzle, an apparatus, and a method for mass production of dual-layer microparticles of a uniform size.

A nozzle for producing microparticles according to the present disclosure includes a nozzle body and a cover. The nozzle body includes a first fluid passageway therein. A plurality of extension tubes is communicated with an end of the first fluid passageway and is spaced from each other. Each of the plurality of extension tubes includes a distant end having an outlet port and located distant to the first fluid passageway. The cover is mounted to the nozzle body and includes a second fluid passageway having an end. A plurality of sleeves is communicated with the end of the second fluid passageway. Each of the plurality of sleeves includes a far end having an opening and located distant to the second fluid passageway. Each of the plurality of extension tubes extends into one of the plurality of sleeves. Each of the plurality of extension tubes has an outer wall spaced from an inner wall of the one of the plurality of sleeves by a spacing. The outlet port of each of the plurality of extension tubes is located between the second fluid passageway and the opening of the one of the plurality of sleeves.

In an example, the plurality of extension tubes and the plurality of sleeves are arranged parallel to each other. Each extension tube is aligned with a corresponding one of the sleeves, such that each extension tube can extend into a corresponding one of the sleeves.

In an example, the second fluid passageway is formed between the cover and the nozzle body, and the plurality of extension tubes of the nozzle body extends through the second fluid passageway. Thus, each extension tube can extend into a corresponding one of the sleeves of the cover.

In an example, the opening of each of the plurality of sleeves and the outlet port of a corresponding one of the plurality of extension tubes have a formation space formed therebetween. The formation space assures that the second fluid at the second openings can completely envelop the first fluid flowing out of the outlet ports.

In an example, the far end of each of the plurality of sleeves having the opening includes a layer of hydrophobic material to prevent the fluid from adhering to the sleeves, reliably avoiding the fluid from accumulating on the openings to thereby reduce an adverse influence on the diameters of the formed microparticle products by the surface tension.

An apparatus for producing microparticles according to the present disclosure includes the above-mentioned nozzle. The apparatus further includes a fluid tank into which the plurality of extension tubes of the nozzle body extends, a fluid interrupting device mounted to the tank and configured to cause disturbance of a fluid received in the fluid tank, and a temperature control system in which the fluid tank is mounted.

In an example, the fluid tank receives a third fluid. The third fluid has a level defining a liquid level. The outlet port of each of the plurality of extension tubes is below the liquid level, such that the opening of each of the plurality of sleeves is located below the liquid level.

In an example, the apparatus for producing microparticles further includes a collection tank. An inlet pipe and an outlet pipe are coupled to the fluid tank and extend through a wall of the fluid tank. The collection tank is intercommunicated with the outlet pipe. A worker can collect the semi-particles of microparticles in the collection tank. Furthermore, the third fluid can be filled into the inlet pipe to maintain the third fluid in the fluid tank at the liquid level, thereby assuring that the opening of each of the plurality of sleeves is located in the third fluid.

In an example, the fluid interrupting device includes a stirring device mounted in the fluid tank. The stirring device can drive the third fluid to flow, and the shear force of the flowing third fluid cuts a dual-layer continuous fluid flowing out of each opening.

In an example, the fluid interrupting device includes a supersonic wave generator mounted to an outer wall of the fluid tank. The supersonic wave generator causes vibrations of the third fluid to interrupt the dual-layer continuous fluid flowing out of each opening.

A method for producing microparticles according to the present disclosure can be carried out by the above apparatus for forming microparticles and includes: filling a third fluid into the fluid tank, with the opening of each of the plurality of sleeves located in the third fluid; filling a first fluid into the first fluid passageway of the nozzle body, making the first fluid flow through the plurality of extension tubes at a first speed, filling a second fluid into the plurality of sleeves of the cover, making the second fluid flow through the plurality of sleeves at a second speed greater than the first speed, with the second fluid enveloping and shearing the first fluid flowing out of the outlet ports of the plurality of extension tubes, forming dual-layer continuous fluids flowing out of the openings of the plurality of sleeves; activating the fluid interrupting device to disturb the third fluid, and making the dual-layer continuous fluids form a plurality of semi-products of microparticles in the fluid tank; collecting the semi-products of microparticles, with each of the plurality of semi-products of microparticles including an inner layer formed by the first fluid, a middle layer formed by the second fluid, and an outer layer formed by the third fluid; and removing the outer layers of the plurality of semi-products of microparticles.

In an example, the second fluid is produced by heating a biodegradable polymer to a glass transition temperature, such that the second fluid can be filled into the second fluid passageway of the nozzle body.

In an example, the temperature control system is activated to maintain the third fluid at a predetermined temperature before the second fluid enters the second fluid passageway, and the predetermined temperature is equal to or lower than the glass transition temperature of the second fluid. Thus, the temperature of the third fluid can assist in curing and shaping of the dual-layer microdroplets while the first and second fluids are forming the dual-layer microdroplets.

In an example, the second fluid is produced by adding an organic solvent into a biodegradable polymer, such that the second fluid can be filled into the first fluid passageway of the nozzle body.

In an example, the first fluid is a liquid containing an active pharmaceutical ingredient. Thus, when the dual-layer microparticle products formed by the first and second fluids are given to an organism, a slow releasing effect of the pharmaceutically active ingredient is achieved by enveloping of the second fluid.

In an example, the first fluid is a gas to form dual-layer microparticle products each of which includes a gaseous inner layer formed by the first fluid.

In an example, the third fluid is a stabilizer. The stabilizer can be a 1-15% polyvinyl acetate solution. The semi-products can be dried or washed by an aqueous solution to remove the outer layers of the semi-products, forming dual-layer microparticle products each of which includes the inner layer and the middle layer of a semi-product.

The nozzle, apparatus, and method for producing microparticles according to the present disclosure use the nozzle body and the cover of the nozzle to generate dual-layer continuous fluids and use the shear force and/or vibrations of the third fluid to interrupt the dual-layer continuous fluids, achieving mass production of dual-layer microparticles of a uniform size while reducing the production time of the dual-layer microparticles, reliably increasing the production efficiency of microparticles.

The present disclosure will become clearer in light of the following detailed description of illustrative embodiments of the present disclosure described in connection with the drawings.

DETAILED DESCRIPTION

Figure 1:
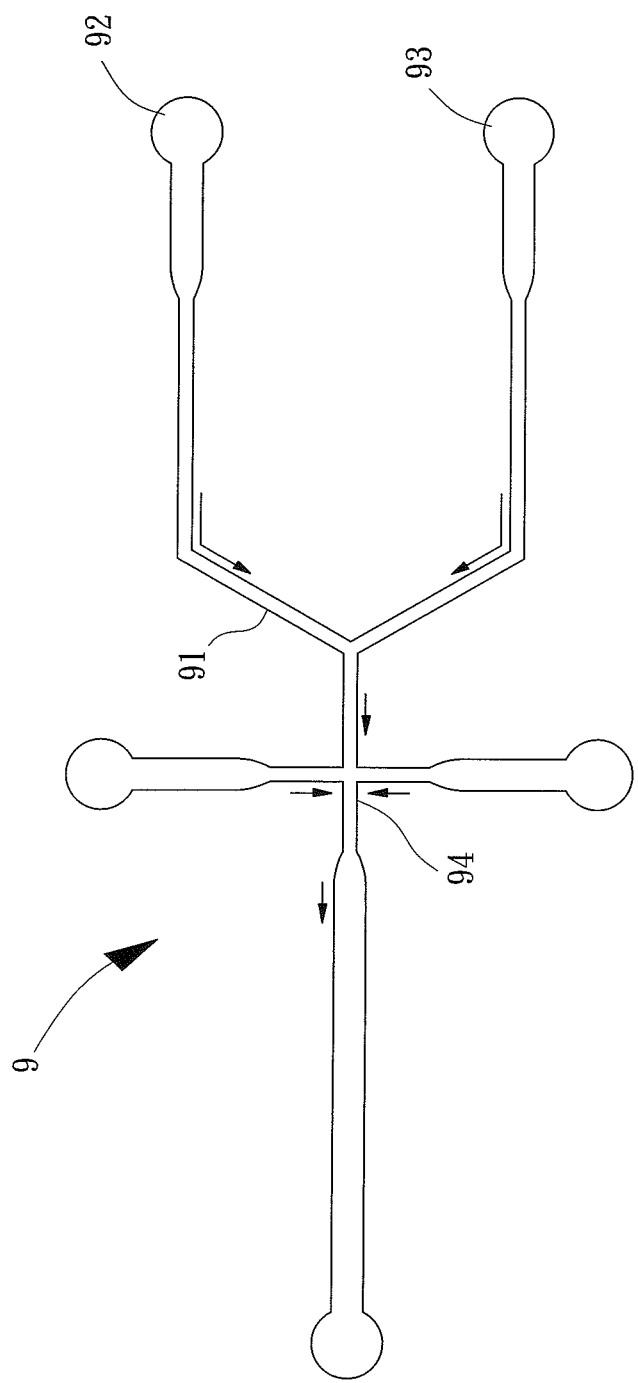
FIG. 1 is a diagrammatic view of a conventional micro fluid passageway structure.
Figure 2:
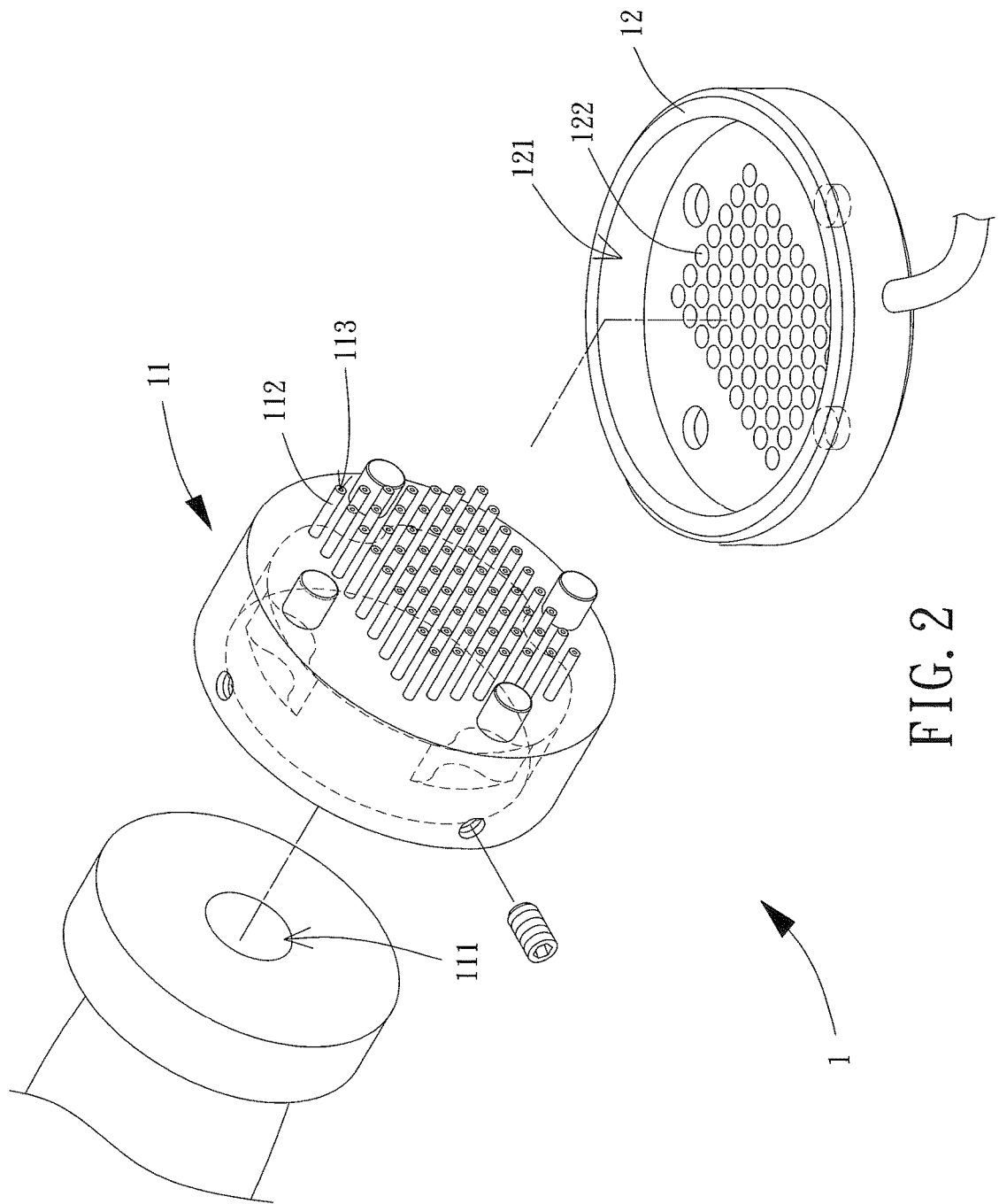
FIG. 2 is an exploded, perspective view illustrating a nozzle for producing microparticles of an embodiment according to the present disclosure.
Figure 3:
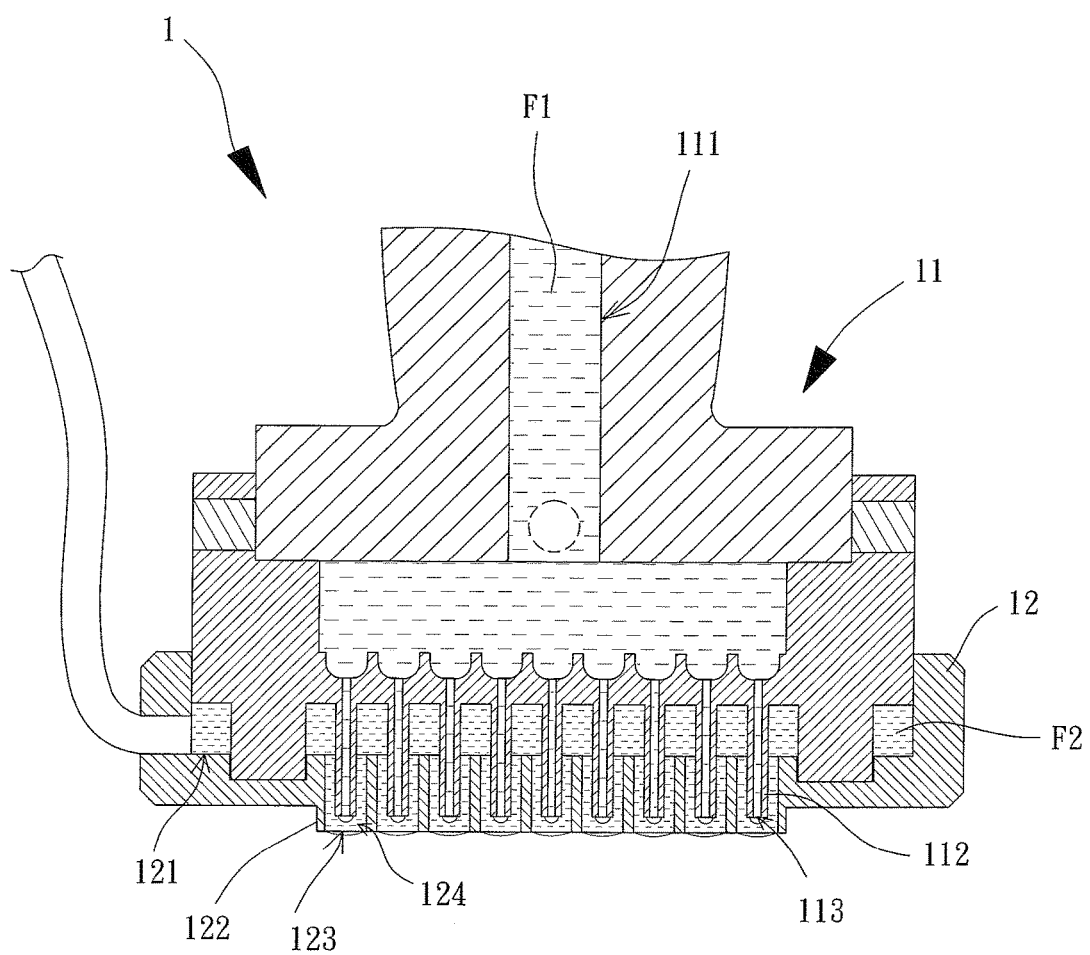
FIG. 3 is a cross sectional view of the nozzle for producing microparticles of FIG. 2.

With reference to FIGS. 2 and 3, a nozzle 1 for producing microparticles of an embodiment according to the present disclosure includes a nozzle body 11 and a cover 12 mounted to the nozzle body 11.

The nozzle body 11 has a first fluid passageway 111 therein. A plurality of extension tubes 112 is communicated with an end of the first fluid passageway 111. The extension tubes 112 are spaced from each other. Each extension tube 112 includes a distant end having an outlet port 113 and located distant to the first fluid passageway 111. The extension tubes 112 can be arranged parallel to each other. The outlet ports 113 of the extension tubes 112 are preferably on the same plane.

The cover 12 includes a second fluid passageway 121. In this non-restrictive embodiment, the second fluid passageway 121 is formed between the cover 12 and the nozzle body 11. Specifically, the cover 12 includes a groove. When the cover 12 is mounted to the nozzle body 11, the groove is located between the cover 12 and the nozzle body 11 and forms the second fluid passageway 121. A plurality of sleeves 122 is communicated with an end of the second fluid passageway 121. Each sleeve 122 includes a far end having an opening 123 and located distant to the second fluid passageway 121. The openings 123 of the sleeves 122 are spaced from each other. The sleeves 122 can be arranged parallel to each other. Furthermore, the outlet ports 113 of the sleeves 122 are preferably on the same plane.

The extension tubes 112 of the nozzle body 11 extend through the second fluid passageway 121. Furthermore, the inner diameter of each sleeve 122 is larger than the outer diameter of each extension tube 112, such that each extension tube 112 can extend into one of the sleeves 122. An outer wall of each extension tube 112 is spaced from an inner wall of the corresponding sleeve 122 by a spacing. The outlet port 113 of each extension tube 112 is located between the second fluid passageway 121 and the opening 123 of a corresponding sleeve 122. The extension tubes 112 and the sleeves 122 can be arranged parallel to each other. Each extension tube 112 is aligned with a corresponding one of the sleeves 122, such that each extension tube 112 can extend into a corresponding one of the sleeves 122.

A first fluid F1 can be filled into the first fluid passageway 111, can flow along the first fluid passageway 111, and can flow out of the nozzle body 11 via the outlet ports 113 of the extension tubes 112. A second fluid F2 can be filled into the second fluid passageway 121, can flow along the second fluid passageway 121, and can flow out of the cover 12 via the openings 123 of the sleeves 122.

In this embodiment, the second fluid F2 is produced by heating a polymer to a glass transition temperature (Tg) or by adding a small amount of organic solvent (such as ethyl acetate, dichloromethane, etc.) into a polymer. The polymer can be a biodegradable polymer including aliphatic polyesters, aliphatic-aromatic copolyesters, polylactide-aliphatic copolyesters, polycaprolactone, polyglutamic acid, polyhydroxy acid ester, or polylactide. More specifically, aliphatic polyesters can be polyglycolic acid, polybutylene succinate butanediamine, or polyethylene succinate. Aliphatic-aromatic copolyesters can be polyethylene terephthalate-polyoxyethylene. Polylactide-aliphatic copolyesters can be polylactic glycolic acid. However, the present disclosure is not limited to these. Other biodegradable polymers used as drug microcarriers can be used as the polymer. In this embodiment, the polymer is preferably polycaprolactone, polylactide, or polylactic glycolic acid. Polycaprolactone has excellent biocompatibility and miscibility and has excellent molecular flowability in the organism due to a low glass transition temperature, presenting excellent permeability for active pharmaceutical ingredients having a low molecular weight.

Figure 4:
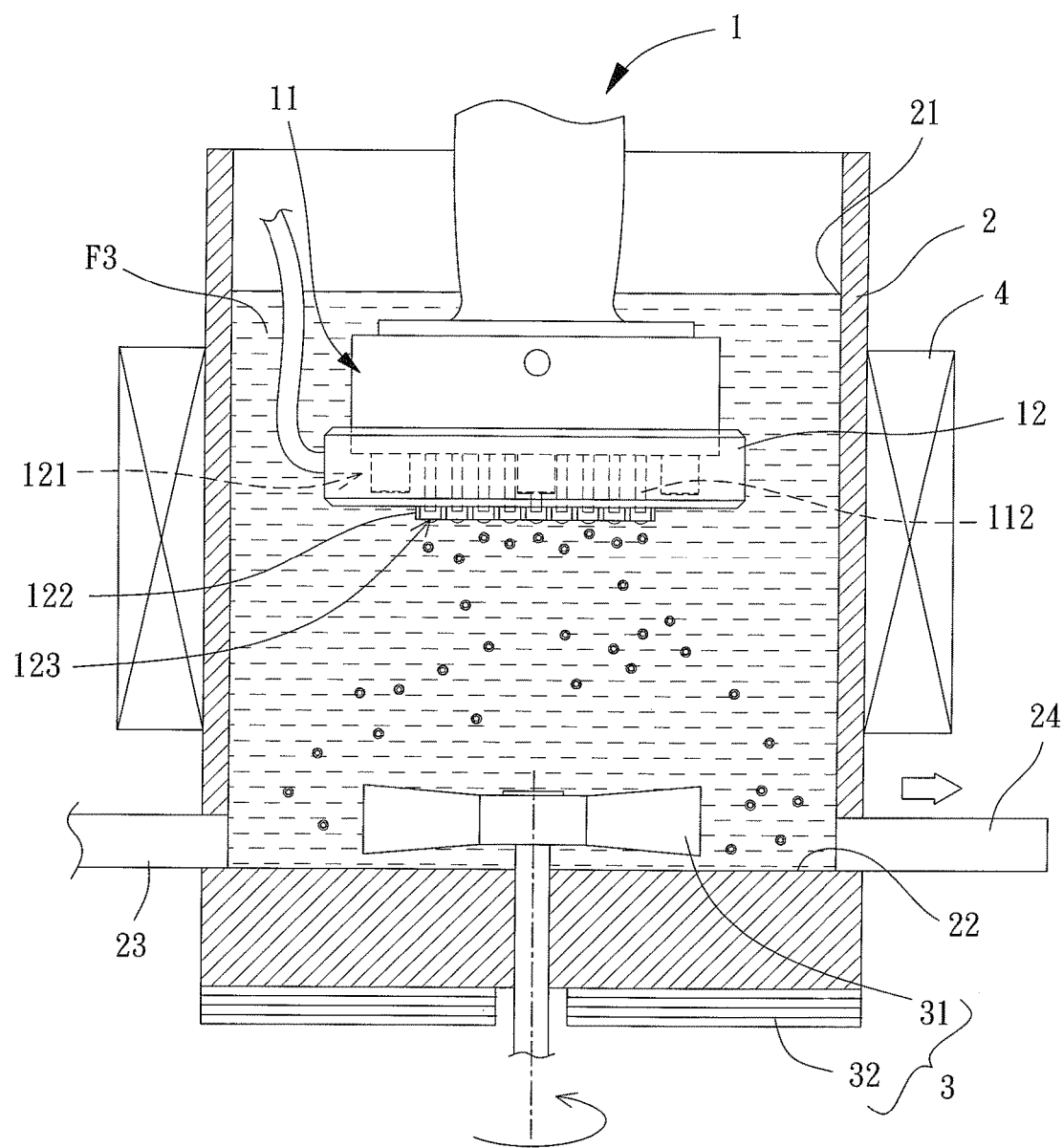
FIG. 4 is a cross sectional view of an apparatus for producing microparticles of an embodiment according to the present disclosure.

With reference to FIG. 4, in practical use of an embodiment according to the present disclosure, the nozzle 1 for producing microparticles can be used in an apparatus for producing microparticles including a fluid tank 2, a fluid interrupting device 3, and a temperature control system 4. The sleeves 122 of the cover 12 extend into the fluid tank 2. The fluid interrupting device 3 is mounted to the fluid tank 2. The fluid interrupting device 3 can include a stirring device 31, a supersonic wave generator 32, or both. In this embodiment, the fluid interrupting device 3 includes both of the stirring device 31 and the supersonic wave generator 32. The stirring device 31 is mounted in the fluid tank 2. The supersonic wave generator 32 is mounted to an outer wall of the fluid tank 2. The fluid tank 2 is mounted in the temperature control system 4.

Specifically, the fluid tank 2 can receive a third fluid F3. The third fluid F3 received in the fluid tank 2 includes a level defining a liquid level 21. The sleeves 122 of the cover 12 extend into the fluid tank 2, such that the opening 123 of each sleeve 122 is located below the liquid level 21. Namely, the openings 123 are located below the liquid level 21 and are, thus, located in the third fluid F3. The fluid interrupting device 3 is used to disturb the third fluid F3 in the fluid tank 2. The stirring device 31 can be driven by a motor to drive the third fluid F3 to flow. The supersonic wave generator 32 can generate high frequency vibrations. For example, the supersonic wave generator 32 is made of piezoelectric material and can include a power capable of generating high frequency electrical energy. The piezoelectric material can turn the high frequency electrical energy into high frequency vibrations which are transmitted through the wall of the fluid tank 2 to the third fluid F3, causing vibrations of the third fluid F3. The temperature control system 4 can control the temperature of the third fluid F3 to maintain the third fluid F3 at a predetermined temperature.

Figure 5:
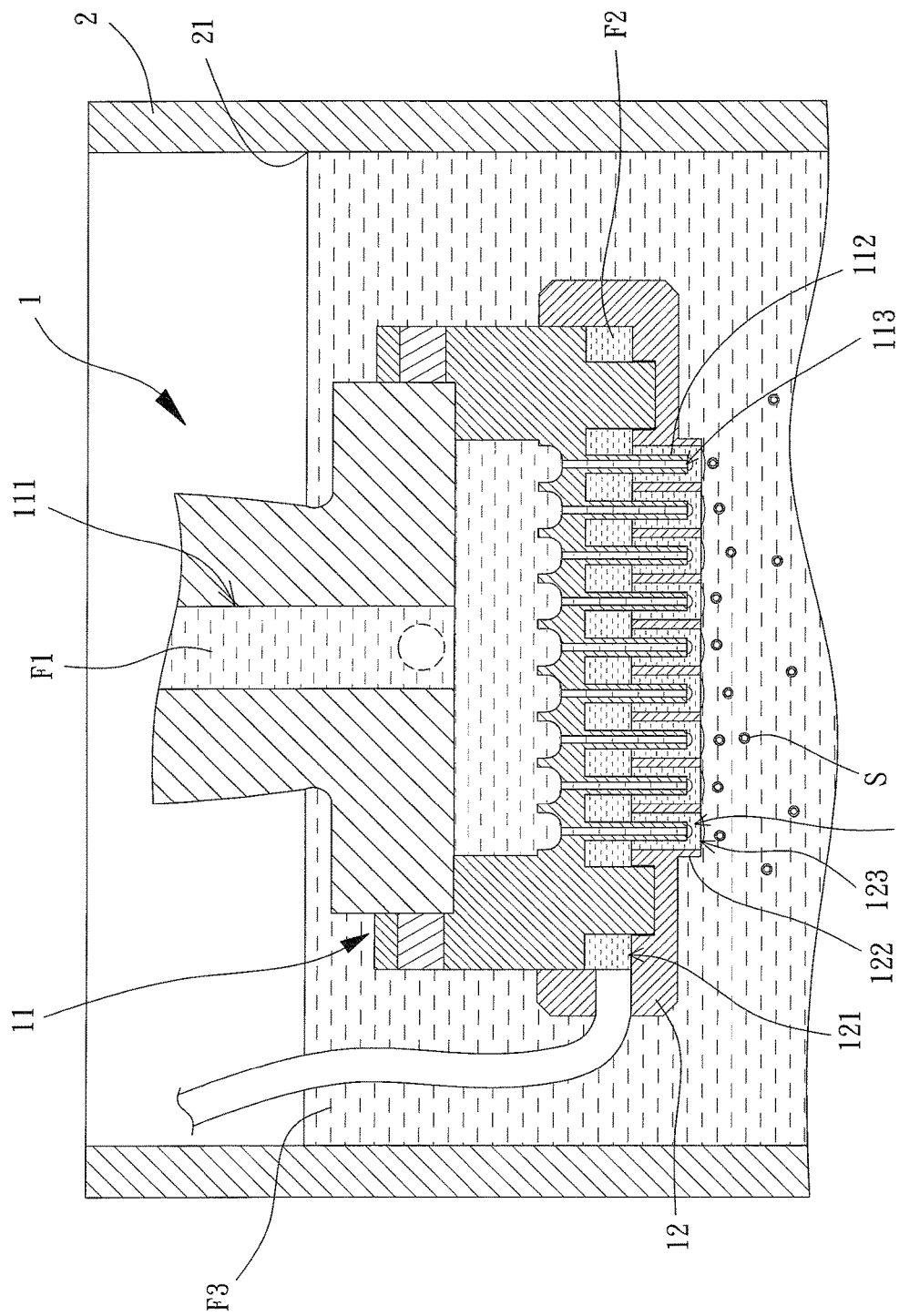
FIG. 5 is an enlarged cross sectional view of a portion of the apparatus of FIG. 4.
Figure 6:
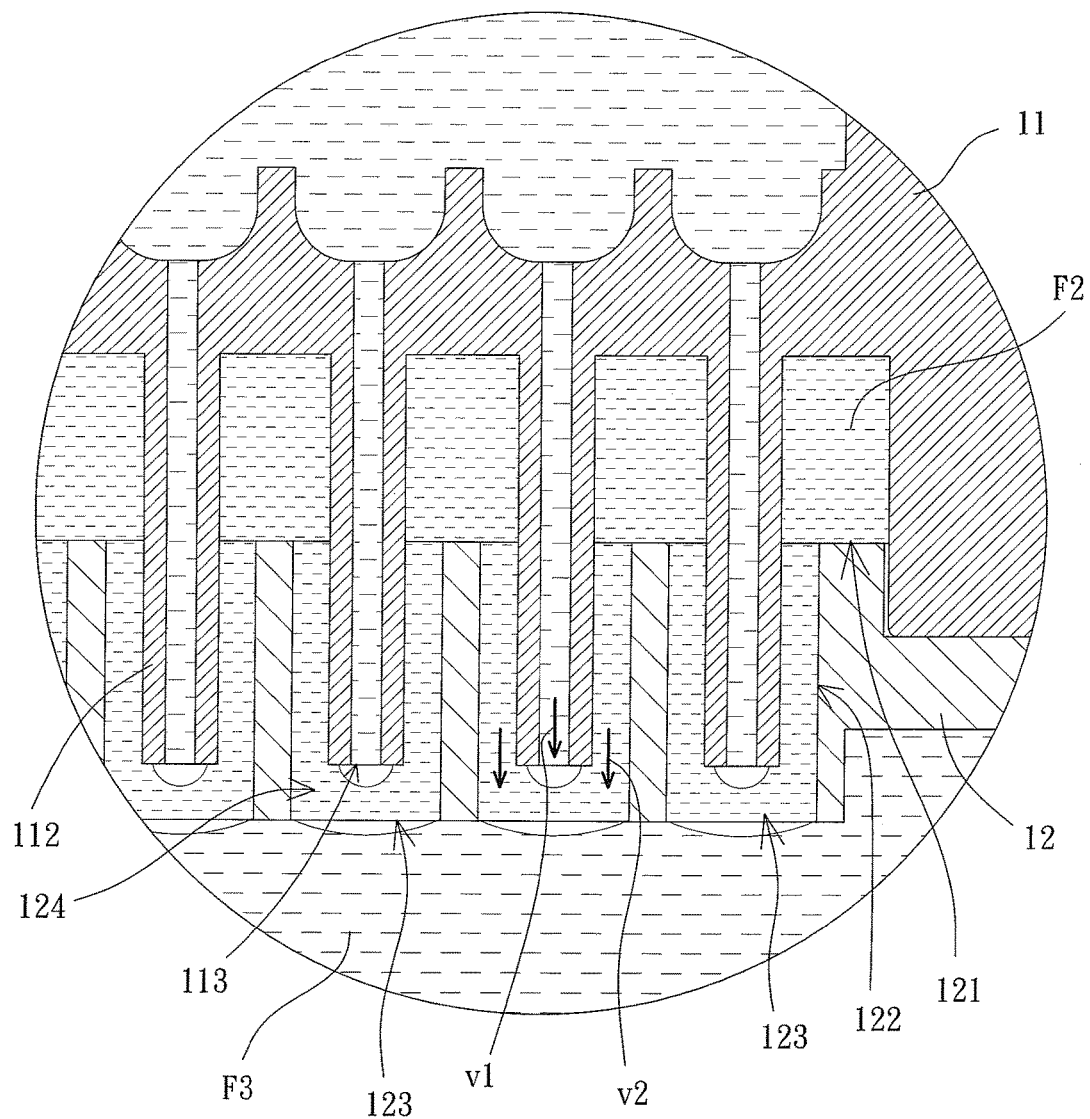
FIG. 6 is an enlarged cross sectional view of a portion of the nozzle of FIG. 5.

With reference to FIGS. 4-6, a method for producing microparticles of an embodiment according to the present disclosure can be carried out by the apparatus for producing microparticles. The method for producing microparticles of this embodiment includes filling the third fluid F3 into the fluid tank 2. The temperature control system 4 is activated to maintain the third fluid F3 at a predetermined temperature. The predetermined temperature is equal to or lower than the glass transition temperature (Tg) of the third fluid F3. In this embodiment, the third fluid F3 can be, but is not limited to, a 1-15% polyvinyl acetate (PVA) solution. The sleeves 122 of the cover 12 extend into the fluid tank 2. The first fluid F1 is filled into the first fluid passageway 111 of the nozzle body 11 and flows out of the nozzle body 11 via the outlet port 113 of each extension tube 112. The second fluid F2 is filled into the second fluid passageway 121, flows through the second fluid passageway 121 and each sleeve 122, and flows out of the cover 12 via the opening 123 of each sleeve 122. The pressures in the first fluid passageway 111 and the second fluid passageway 121 are controlled to make the first fluid F1 flow through the extension tubes 112 at a first speed v1 and to make the second fluid F2 flow through the sleeves 122 at a second speed v2. Since the outlet port 113 of each extension tube 112 is located between the second fluid passageway 121 and the opening 123 of each sleeve 122, by making the second speed v2 greater than the first speed v1, a shear force can be created by the difference between the first speed v1 and the second speed v2, such that the second fluid F2 envelops and shears the first fluid F1 flowing out of the outlet ports 113, forming dual-layer continuous fluids at the openings 123. The inner layer and the outer layer of each dual-layer continuous fluid are the first fluid F1 and the second fluid F2, respectively. The dual-layer continuous fluids flow out of the cover 12 via the openings 123 of the sleeves 122.

Figure 7:
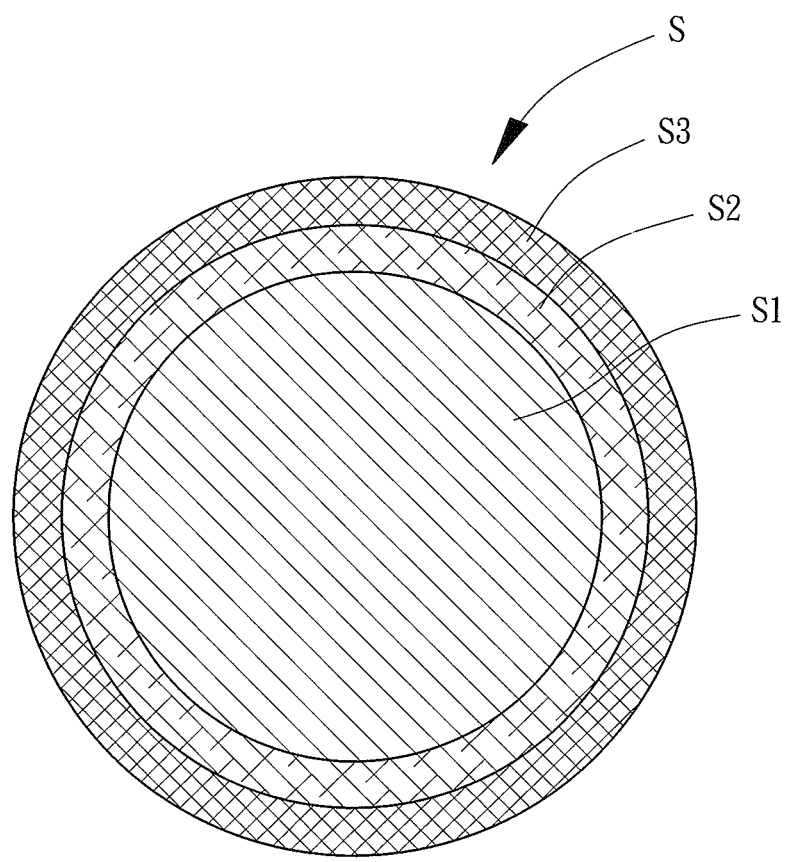
FIG. 7 is a diagrammatic view of an example of a semi-product of a microparticle produced by the apparatus of FIG. 4.

Next, the fluid interrupting device 3 is activated to disturb the third fluid F3 in the fluid tank 2, thereby interrupting the dual-layer continuous fluids. Specifically, in this embodiment in which the fluid interrupting device 3 includes both of the stirring device 31 and the supersonic wave generator 32, activation of the fluid interrupting device 3 includes rotating the stirring device 31 and/or activating the supersonic wave generator 32. The stirring device 31 can drive the third fluid F3 to flow, using the shear force generated resulting from the flowing third fluid F3 to cut the dual-layer continuous fluids flowing out of the cover 12, such that the dual-layer continuous fluids form dual-layer microdroplets. Alternatively, the supersonic wave generator 32 causes the third fluid F3 to vibrate for interrupting the dual-layer continuous fluids flowing out of the cover 12, such that the dual-layer continuous fluids form dual-layer microdroplets. Also, the supersonic wave generator 32 causes the third fluid F3 to vibrate for controlling the diameter of the formed dual-layer microdroplets. At this time, the third fluid F3 received in the fluid tank 2 envelops the outer layers of the dual-layer microdroplets (namely, emulsification) to assist in curing and shaping of the dual-layer microdroplets, thereby forming semi-products S of microparticles in the fluid tank 2, as shown in FIG. 7. Each semi-product S includes an inner layer S1 formed by the first fluid F1, a middle layer S2 formed by the second fluid F2, and an outer layer S3 formed by the third fluid F3.

Figure 8:
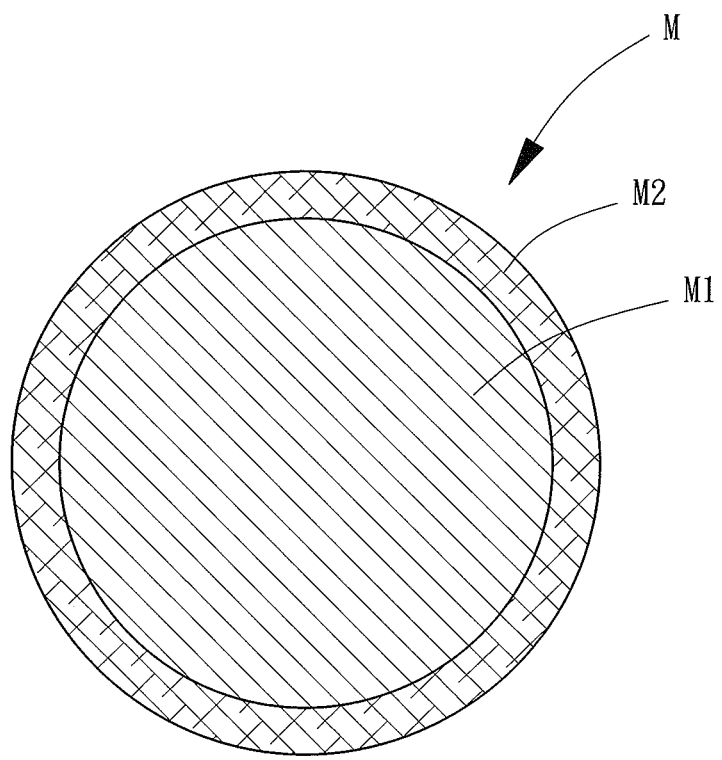
FIG. 8 is a diagrammatic view of a dual-layer microparticle product of FIG. 7.
Figure 9:
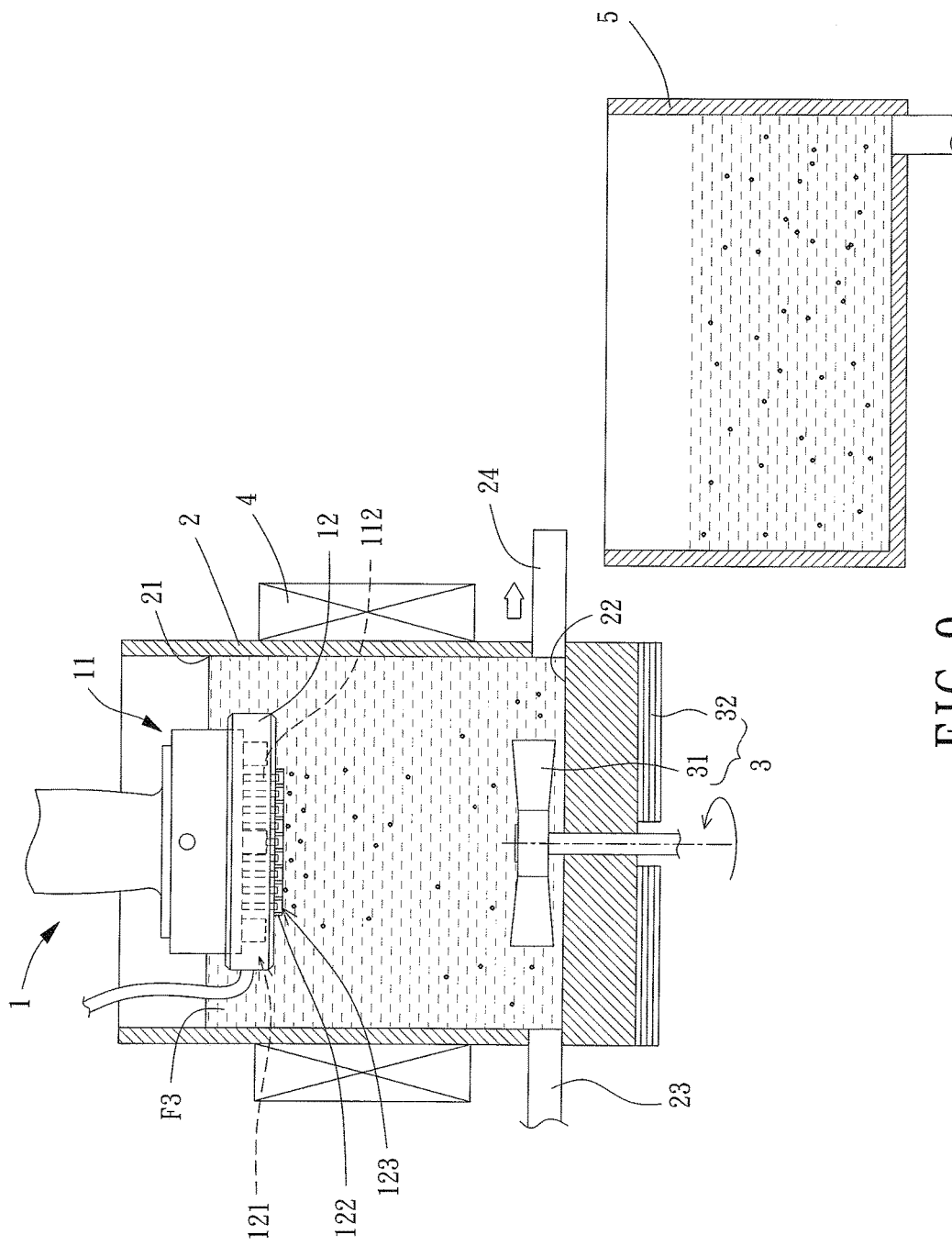
FIG. 9 is a diagrammatic view illustrating an apparatus for producing microparticles of another example according to the present disclosure, with the apparatus including a collection tank.

Finally, the semi-products S are collected, and the outer layers S3 formed by the third fluid F3 are removed to form dual-layer microparticle products M each of which only includes the inner layer M1 formed by the first fluid F1 and the outer layer M2 formed by the second fluid F2 (see FIG. 8). For example, the semi-products S are dried (such as by hot air) to evaporate the outer layers S3. Alternatively, the semi-products S are washed by an aqueous solution to remove the outer layers S3, forming the dual-layer microparticle products M. The worker can collect the semi-products S by using the fluid tank 2. Alternatively, as shown in FIGS. 4 and 9, in this embodiment, an inlet pipe 23 and an outlet pipe 24 are coupled to the fluid tank 2 and extend through a wall of the fluid tank 2. Preferably, the outlet pipe 24 is mounted to a position adjacent to the bottom 22. The apparatus for producing microparticles can further include a collection tank 5 intercommunicated with the outlet pipe 24 of the fluid tank 2. Thus, the third fluid F3 along with the semi-products S can flow through the outlet pipe 24 into the collection tank 5, and a worker can collect the semi-product S in the collection tank 5. Furthermore, the third fluid F3 can be filled into the inlet pipe 23 to maintain the third fluid F3 in the fluid tank 2 at the liquid level 21, thereby assuring that the opening 123 of each sleeve 122 is located in the third fluid F3.

The nozzle 1, apparatus, and method according to the present disclosure use the nozzle body 11 and the cover 12 of the nozzle 1 to generate dual-layer continuous fluids and use the shear force and/or the vibrations of the third fluid F3 to interrupt the dual-layer continuous fluids, thereby forming a large number of semi-products S for subsequent production of the dual-layer microparticle products M. In comparison with the conventional micro fluid passageway structure 9 that requires a troublesome procedure to form the microparticles and that forms only one microparticle at a time, the nozzle 1, apparatus, and method according to the present disclosure can achieve mass production of dual-layer microparticles of a uniform diameter and can reduce the production time of the dual-layer microparticles, increasing the production efficiency of the microparticles.

Furthermore, the apparatus and method for producing microparticles according to the present disclosure use the shear force and/or vibrations of the third fluid F3 to interrupt the dual-layer continuous fluids. The rotational speed of the stirring device 31 can be adjusted to control the shear force of the third fluid F3. Alternatively, the frequency and amplitude of the supersonic wave generator 32 can be adjusted to control the vibrations of the third fluid F3. Thus, precise control of the diameters of the dual-layer microparticle products M can be achieved. For example, when the first fluid F1 filled into the first passageway 111 or the second fluid F2 filled into the second fluid passageway 121 has a high concentration, the rotational speed of the stirring device 31 or the amplitude of the supersonic wave generator 32 can be increased to assure that the third fluid F3 can effectively interrupt the dual-layer continuous fluids, avoiding the diameters of the formed dual-layer microparticle products M from being adversely affected by the concentration of the first or second fluid F1, F2 and thereby precisely controlling the diameters of the formed dual-layer microparticle products M. Thus, the nozzle 1, apparatus, and method for producing microparticles according to the present disclosure can increase the precision of the diameters of the microparticles.

Furthermore, the third fluid F3 can be a stabilizer, such as the above-mentioned polyvinyl acetate (PVA) solution. When the dual-layer continuous fluids are interrupted to form dual-layer microdroplets, the third fluid F3 provides an isolating effect to avoid the dual-layer microdroplets formed by the first fluid F1 and the second fluid F2 from aggregating in the third fluid F3. Furthermore, by using the stirring device 31 to drive the third fluid F3 to flow and/or by using the supersonic wave generator 32 to vibrate the third fluid F3, the dual-layer microdroplets are prevented from aggregating in the third fluid F3. Accordingly, the apparatus and method for producing microparticles according to the present disclosure can assure each dual-layer microdroplet is enveloped by the third fluid F3, increasing the yield of microparticles.

According to the above technical concept, the features of the nozzle 1, apparatus, and method for producing microparticles according to the present disclosure will be described hereinafter.

With reference to FIG. 6, to make the second fluid F2 at each opening 123 completely envelop the first fluid F1 flowing out of the corresponding outlet port 113, the opening 123 of each sleeve 122 is preferably spaced from the outlet port 113 of the corresponding extension tube 112 by a spacing, such that the opening 123 of each sleeve 122 and the outlet port 113 of the corresponding extension tube 112 have a formation space 124 formed therebetween. The size of the formation space 124 can be adjusted by the difference between the surface tension of the first fluid F1 and the surface tension of the second fluid F2, assuring that the second fluid F2 at the openings 123 can completely envelop the first fluid F1 flowing out of the outlet ports 113.

As mentioned above, the method for producing microparticles of an embodiment according to the present disclosure can respectively control the pressures of the first and second fluids F1 and F2 to make the first and second fluids F1 and F2 respectively flow through the extension tubes 112 and the sleeves 122 at the first and second speeds v1 and v2, forming dual-layer continuous fluids that are driven into the third fluid F3 via the openings 123 of the cover 12. With reference to FIG. 4, in this embodiment, the cover 12 extends from a horizontal, upper position of the fluid tank 2 into the fluid tank 2 of the apparatus for producing microparticles. Alternatively, with reference to FIG. 10, in some embodiments according to the present disclosure, the cover 12 extends from a horizontal, lower position of the fluid tank 2 into the fluid tank 2. Similarly, in other embodiments according to the present disclosure, the cover 12 can extend from another horizontal position of the fluid tank 2 into the fluid tank 2. Namely, the relative position between the cover 12 and the fluid tank 2 is not limited in the present disclosure as long as the opening 123 of each sleeve 122 is below the liquid level 21 to permit the dual-layer continuous fluids to be driven into the third fluid F3.

Figure 10:
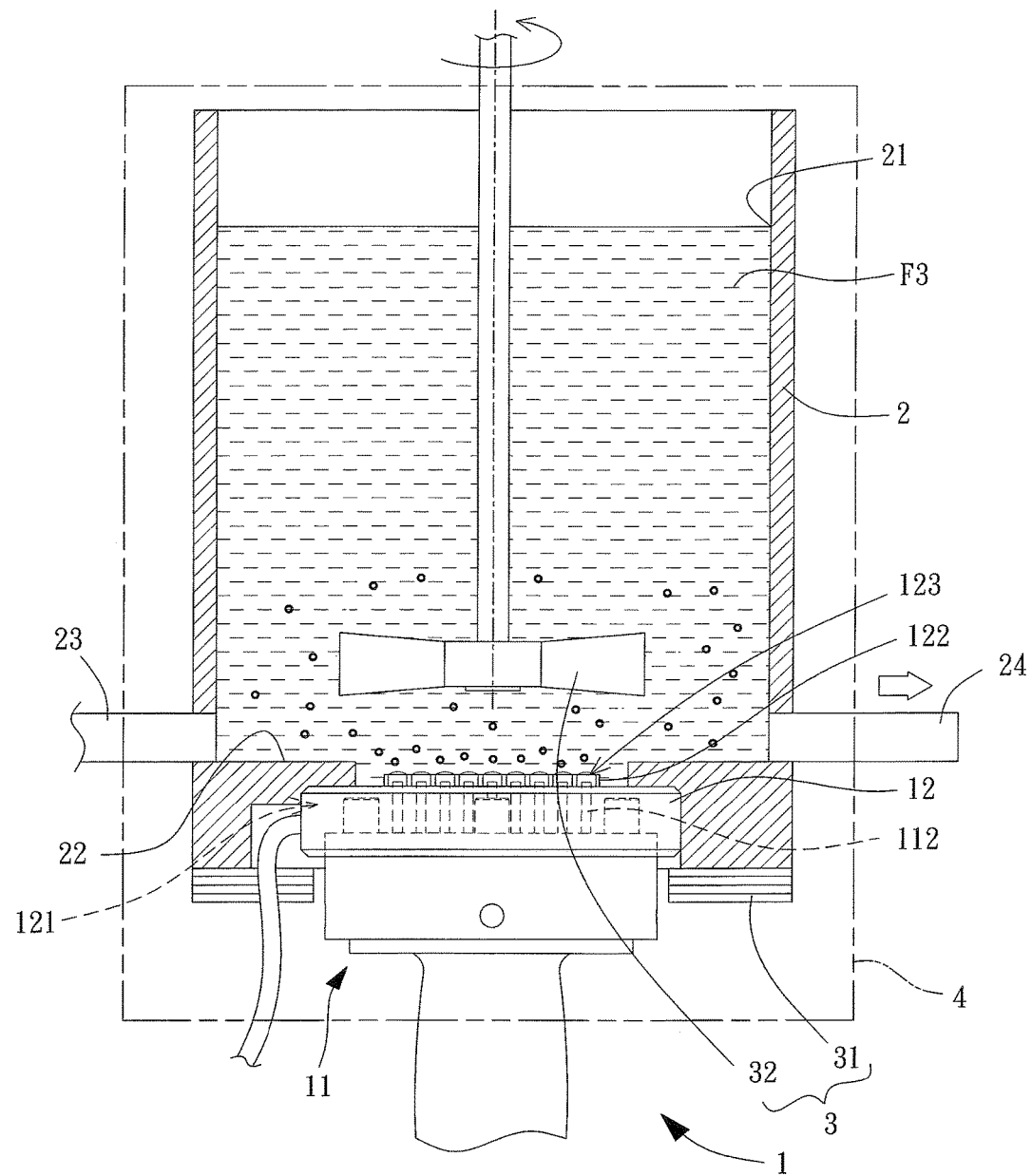
FIG. 10 is a cross sectional view of an apparatus for producing microparticles of another embodiment according to the present disclosure.

Furthermore, with reference to FIG. 4, in this embodiment, the temperature control system 4 can be a heating coil and is coupled to the outer wall of the fluid tank 2. Thus, the temperature control system 4 can heat the third fluid F3 via the outer wall of the fluid tank 2 to maintain the third fluid F3 at the predetermined temperature. Alternatively, as shown in FIG. 10, in some embodiments according to the present disclosure, the temperature control system 4 can be a thermostat box, and the fluid tank 2 can be mounted in the temperature control system 4. Thus, the temperature control system 4 can also maintain the third fluid F3 at the predetermined temperature.

In the method for producing microparticles of an embodiment according to the present disclosure, the temperature control system 4 is activated to maintain the third fluid F3 at the predetermined temperature, such that the temperature of the third fluid F3 can assist in curing and shaping of the microdroplets while the first fluid F1 and the second fluid F2 are forming the microdroplets. Nevertheless, as mentioned above, the second fluid F2 can be produced by adding a small amount of organic solvent into a polymer. Thus, in some cases, curing and shaping of the microdroplets formed by the first fluid F1 and the second fluid F2 may not be significantly related to the temperature of the third fluid F3. Consequently, the temperature control system 4 does not have to be activated in the method for producing microparticles in some embodiments according to the present disclosure.

Figure 11:
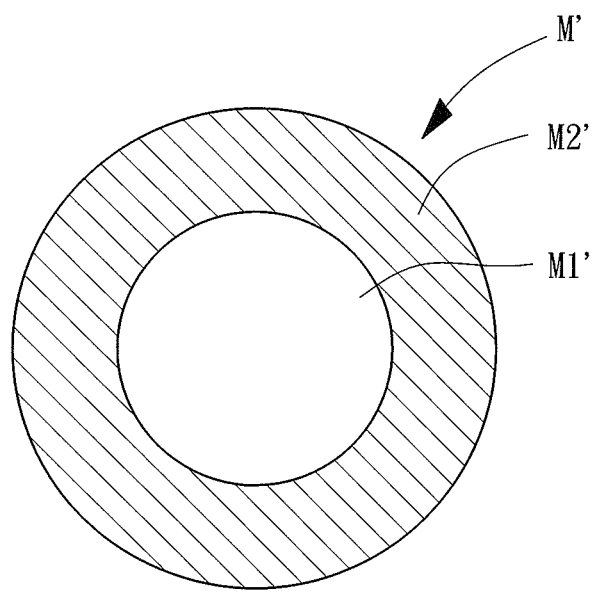
FIG. 11 is a diagrammatic view of a dual-layer microparticle product produced by the apparatus of FIG. 10, with the microparticle product including a gaseous inner layer.

Furthermore, the first fluid F1 can be a liquid containing a active pharmaceutical ingredient, such as 1,3-bis(2-chloroethyl)-1-nitrosourea (BCNU) or doxorubicin (DOX). Thus, when the dual-layer microparticle products M formed by the first and second fluids F1 and F2 are given to an organism, a slow releasing effect of the active pharmaceutical ingredient is achieved by enveloping of the second fluid F2. Alternatively, in some embodiments according to the present disclosure, a gas can be used as the first fluid F1 to form the dual-layer microparticle products M' (see FIG. 11). Each dual-layer microparticle product M' includes a gaseous inner layer M1' formed by the first fluid F1.

In some embodiments according to the present disclosure, the far end of each sleeve 122 having the opening 123 includes a layer of hydrophobic material. The hydrophobic material can be, but is not limited to, silicon dioxide (SiO2) or titanium dioxide (TiO2). As a non-restrictive example, the layer of hydrophobic material is disposed on the far end of each sleeve 122 having the opening 123 by plating. By providing the hydrophobic material on the opening 123 of each sleeve 122, the dual-layer continuous fluids come in contact with the layer of hydrophobic material when flowing out of each opening 123, such that the dual-layer continuous fluids are difficult to adhere to the sleeves 122, reliably preventing the dual-layer continuous fluids from accumulating on the openings 123 to more effectively reduce the adverse influence on the diameters of the formed dual-layer microparticle products M by the surface tension.

In view of the foregoing, the nozzle 1, method, and apparatus for producing microparticles according to the present disclosure use the nozzle body 11 and the cover 12 of the nozzle 1 to generate dual-layer continuous fluids and use the shear force and/or vibrations of the third fluid F3 to interrupt the dual-layer continuous fluids, achieving mass production of semi-products S of microparticles. Thus, mass production of dual-layer microparticles of a uniform size can be achieved while reducing the production time of the dual-layer microparticles, reliably increasing the production efficiency of microparticles.

Furthermore, the apparatus and method for producing microparticles according to the present disclosure use the shear force and/or vibrations of the third fluid F3 to interrupt the dual-layer continuous fluids. The rotational speed of the stirring device 31 can be adjusted to control the shear force of the third fluid F3. Alternatively, the frequency and amplitude of the supersonic wave generator 32 can be adjusted to control the vibrations of the third fluid F3. Accordingly, precise control of the diameters of the formed dual-layer microparticle products M can be achieved. Furthermore, the present disclosure is suitable for producing microparticles from a second fluid F2 with a high concentration, reliably increasing the control precision of the diameters of the microparticles.

Furthermore, the third fluid F3 provides an isolating effect to avoid the dual-layer microdroplets formed by the first fluid F1 and the second fluid F2 from aggregating in the third fluid F3. Furthermore, by using the stirring device 31 to drive the third fluid F3 to flow and/or by using the supersonic wave generator 32 to vibrate the third fluid F3, the dual-layer microdroplets are prevented from aggregating in the third fluid F3. Accordingly, the apparatus and method for producing microparticles according to the present disclosure can assure each dual-layer microdroplet is enveloped by the third fluid F3, increasing the yield of microparticles.

Thus since the present disclosure disclosed herein may be embodied in other specific forms without departing from the spirit or general characteristics thereof, some of which forms have been indicated, the embodiments described herein are to be considered in all respects illustrative and not restrictive. The scope of the present disclosure is to be indicated by the appended claims, rather than by the foregoing description, and all changes which come within the meaning and range of equivalency of the claims are intended to be embraced therein.

What is claimed is:

1. A nozzle for producing microparticles, comprising:
a nozzle body including a first fluid passageway therein, with a plurality of extension tubes communicated with an end of the first fluid passageway and spaced from each other, with each of the plurality of extension tubes including a distant end having an outlet port and located distant to the first fluid passageway; and
a cover mounted to the nozzle body and including a second fluid passageway having an end, with a plurality of sleeves communicated with the end of the second fluid passageway, with each of the plurality of sleeves including a far end having an opening and located distant to the second fluid passageway, wherein the nozzle body and the cover are detachable from each other,
with each of the plurality of extension tubes extending into one of the plurality of sleeves, with each of the plurality of extension tubes having an outer wall spaced from an inner wall of the one of the plurality of sleeves by a spacing, with the outlet port of each of the plurality of extension tubes located between the second fluid passageway and the opening of the one of the plurality of sleeves.

2. A nozzle for producing microparticles comprising:
a nozzle body including a first fluid passageway therein, with a plurality of extension tubes communicated with an end of the first fluid passageway and spaced from each other, with each of the plurality of extension tubes including a distant end having an outlet port and located distant to the first fluid passageway; and
a cover mounted to the nozzle body and including a second fluid passageway having an end, with a plurality of sleeves communicated with the end of the second fluid passageway, with each of the plurality of sleeves including a far end having an opening and located distant to the second fluid passageway,
with each of the plurality of extension tubes extending into one of the plurality of sleeves, with each of the plurality of extension tubes having an outer wall spaced from an inner wall of the one of the plurality of sleeves by a spacing, with the outlet port of each of the plurality of extension tubes located between the second fluid passageway and the opening of the one of the plurality of sleeves,
wherein the far end of each of the plurality of sleeves having the opening includes a layer of hydrophobic material.

3. The nozzle for producing microparticles as claimed in claim 2, wherein the plurality of extension tubes and the plurality of sleeves are arranged parallel to each other.

4. The nozzle for producing microparticles as claimed in claim 2, wherein the second fluid passageway is formed between the cover and the nozzle body, and wherein the plurality of extension tubes of the nozzle body extends through the second fluid passageway.

5. The nozzle for producing microparticles as claimed in claim 2, wherein the opening of each of the plurality of sleeves and the outlet port of a corresponding one of the plurality of extension tubes have a formation space formed therebetween.

6. An apparatus comprising:
a nozzle for producing microparticles, with the nozzle including a nozzle body and a cover, with the nozzle body including a first fluid passageway therein, with a plurality of extension tubes communicated with an end of the first fluid passageway and spaced from each other, with each of the plurality of extension tubes including a distant end having an outlet port and located distant to the first fluid passageway, with the cover mounted to the nozzle body and including a second fluid passageway having an end, with a plurality of sleeves communicated with the end of the second fluid passageway, with each of the plurality of sleeves including a far end having an opening and located distant to the second fluid passageway, with each of the plurality of extension tubes extending into one of the plurality of sleeves, with each of the plurality of extension tubes having an outer wall spaced from an inner wall of the one of the plurality of sleeves by a spacing, with the outlet port of each of the plurality of extension tubes located between the second fluid passageway and the opening of the one of the plurality of sleeves;
a fluid tank, with the plurality of extension tubes of the nozzle body extending into the fluid tank;

a fluid interrupting device mounted to the tank, with the fluid interrupting device configured to cause disturbance of a fluid received in the fluid tank; and a temperature control system, with the fluid tank mounted in the temperature control system.

7. The apparatus as claimed in claim 6, with a third fluid received in the fluid tank including a level defining a liquid level, and with the opening of each of the plurality of sleeves located below the liquid level.

8. The apparatus as claimed in claim 6, further comprising a collection tank, with an inlet pipe and an outlet pipe coupled to the fluid tank and extending through a wall of the fluid tank, and with the collection tank intercommunicated with the outlet pipe.

9. The apparatus as claimed in claim 6, wherein the fluid interrupting device includes a stirring device mounted in the fluid tank.

10. The apparatus as claimed in claim 6, wherein the fluid interrupting device includes a supersonic wave generator mounted to an outer wall of the fluid tank.

11. A method for producing microparticles using the apparatus as claimed in claim 6, with the method comprising:

filling a first fluid into the first fluid passageway of the nozzle body, making the first fluid flow through the plurality of extension tubes at a first speed, filling a second fluid into the plurality of sleeves of the cover, making the second fluid flow through the plurality of sleeves at a second speed greater than the first speed, with the second fluid enveloping and shearing the first fluid flowing out of the outlet ports of the plurality of extension tubes, forming dual-layer continuous fluids flowing out of the openings of the plurality of sleeves, filling a third fluid into the fluid tank, with the opening of each of the plurality of sleeves located in the third fluid;

activating the fluid interrupting device to disturb the third fluid, and making the dual-layer continuous fluids form a plurality of semi-products of microparticles in the fluid tank;

collecting the semi-products of microparticles, with each of the plurality of semi-products of microparticles including an inner layer formed by the first fluid, a middle layer formed by the second fluid, and an outer layer formed by the third fluid; and removing the outer layers of the plurality of semi-products of microparticles.

12. The method for producing microparticles as claimed in claim 11, further comprising producing the second fluid by heating a biodegradable polymer to a glass transition temperature.

13. The method for producing microparticles as claimed in claim 12, further comprising activating the temperature control system to maintain the third fluid at a predetermined temperature before the second fluid enters the second fluid passageway, wherein the predetermined temperature is equal to or lower than the glass transition temperature of the second fluid.

14. The method for producing microparticles as claimed in claim 11, further comprising producing the second fluid by adding an organic solvent into a biodegradable polymer.

15. The method for producing microparticles as claimed in claim 11, wherein the first fluid is a liquid containing an active pharmaceutical ingredient.

16. The method for producing microparticles as claimed in claim 11, wherein the first fluid is a gas.

17. The method for producing microparticles as claimed in claim 11, wherein the third fluid is a stabilizer.

18. The method for producing microparticles as claimed in claim 17, wherein the stabilizer is a 1-15% polyvinyl acetate solution.

19. The method for producing microparticles as claimed in claim 11, further comprising processing the plurality of semi-products of microparticles by drying or by washing by an aqueous solution to remove the outer layers of the plurality of semi-products.

* * * * *